(12) United States Patent
Samsami

(10) Patent No.: US 10,376,249 B1
(45) Date of Patent: Aug. 13, 2019

(54) CERVICAL TISSUE SAMPLE DEVICE

(71) Applicant: David Samsami, Honolulu, HI (US)

(72) Inventor: David Samsami, Honolulu, HI (US)

( * ) Notice: Subject to any disclaimer, the term of this patent is extended or adjusted under 35 U.S.C. 154(b) by 0 days.

(21) Appl. No.: 16/260,241

(22) Filed: Jan. 29, 2019

Related U.S. Application Data

(60) Provisional application No. 62/627,881, filed on Feb. 8, 2018.

(51) Int. Cl.
*A61B 5/00* (2006.01)
*A61B 10/02* (2006.01)
*A61B 10/00* (2006.01)

(52) U.S. Cl.
CPC .. *A61B 10/0291* (2013.01); *A61B 2010/0074* (2013.01); *A61B 2010/0216* (2013.01)

(58) Field of Classification Search
CPC ................ A61B 10/02; A61B 10/0291; A61B 2010/0216
USPC ................................................. 600/569, 572
See application file for complete search history.

(56) References Cited

U.S. PATENT DOCUMENTS

| | | |
|---|---|---|
| 4,862,899 A | 9/1989 | Bucaro |
| 5,445,164 A | 8/1995 | Worthen et al. |
| 5,787,891 A | 8/1998 | Sak |
| 5,792,074 A * | 8/1998 | Turkel .................. A61B 10/02 600/569 |
| 5,795,309 A * | 8/1998 | Leet .................. A61B 10/0291 600/569 |
| 5,823,954 A * | 10/1998 | Chaffringeon ..... A61B 10/0045 600/367 |
| 6,036,658 A * | 3/2000 | Leet .................. A61B 10/0291 600/569 |
| 6,336,905 B1 * | 1/2002 | Colaianni .......... A61B 10/0291 600/569 |
| 6,352,513 B1 * | 3/2002 | Anderson .......... A61B 10/0045 600/569 |
| 6,475,165 B1 | 11/2002 | Fournier |
| 8,801,628 B2 | 8/2014 | Teschendorf |
| 9,186,129 B2 * | 11/2015 | Blitzer ................... A61B 10/02 |
| 10,149,667 B2 * | 12/2018 | Chin-Ly ............ A61B 10/0291 |

* cited by examiner

*Primary Examiner* — Max F Hindenburg
(74) *Attorney, Agent, or Firm* — Global Intellectual Property Agency, LLC; David Boudwin

(57) ABSTRACT

A cervical tissue sample device for extracting cells from the cervix. A cervical tissue sample device includes a plunger slidably disposed along a longitudinal axis within a barrel. The plunger has a first end with a seal thereon and a second end which includes a plunger flange. A plurality of bristles extends longitudinally from the seal of the plunger. The barrel has a first end with an opening thereon such that the plurality of bristles is exposed therethrough when the plunger is depressed. An outer shroud is disposed about a perimeter of the first end of the plunger and configured to encapsulate the plurality of bristles therein when the plurality of bristles is disposed within the barrel. In this way, a user is able to collect a cervical tissue sample without utilizing a medical professional to extract the cells from the cervix.

6 Claims, 3 Drawing Sheets

US 10,376,249 B1

CERVICAL TISSUE SAMPLE DEVICE

CROSS REFERENCE TO RELATED APPLICATIONS

This application claims the benefit of U.S. Provisional Application No. 62/627,881 filed on Feb. 8, 2018. The above identified patent application is herein incorporated by reference in its entirety to provide continuity of disclosure.

BACKGROUND OF THE INVENTION

The present invention relates to cervical tissue sample devices. More specifically, the invention provides a syringe with a barrel and a plunger, with a plurality of bristles disposed thereon the plunger and configured to extend from the barrel when the plunger is depressed. The plurality of bristles is protected by a shroud within the barrel.

Many women fall victim to cervical cancer every year. However, early stage cervical cancer can easily be detected and quickly treated when examining cervical cell changes through a routine pap smear, wherein a medical professional will extract a collection of cervical tissue cells to test. Despite this, many women do not get a routine pap smear, as it can be an embarrassing and painful process. Additionally, these tissue samples can also be used to test for some forms of sexually transmitted diseases, such as *chlamydia*, gonorrhea, or HPV. Thus, an improved cervical tissue sample device that can efficiently collect a cervical tissue sample without utilizing a medical professional to extract the cells from the cervix is desired.

SUMMARY OF THE INVENTION

In view of the foregoing disadvantages inherent in the known types of cervical tissue sample devices now present in the known art, the present invention provides a cervical tissue sample device wherein the same can be utilized for providing convenience for the user when desiring to easily collect a cervical tissue sample without utilizing a medical professional to extract the cells from the cervix.

The present system comprises a cervical tissue sample device. The cervical tissue sample device comprises a syringe, having a plunger slidably disposed within a barrel, wherein the plunger is configured to slide along a longitudinal axis within the barrel. The plunger has a first end and a second end, wherein the first end has a seal disposed thereon and the second end comprises a plunger flange. A plurality of bristles extends from the seal of the plunger along the longitudinal axis. The barrel has a first end and a second end, wherein the first end has an opening thereon such that the plurality of bristles is exposed therethrough when the plunger is depressed. An outer shroud is disposed about a perimeter of the first end of the plunger and configured to encapsulate the plurality of bristles therein when the plurality of bristles is disposed within the barrel. In this way, a user is able to collect a cervical tissue sample without utilizing a medical professional to extract the cells from the cervix.

BRIEF DESCRIPTION OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1:
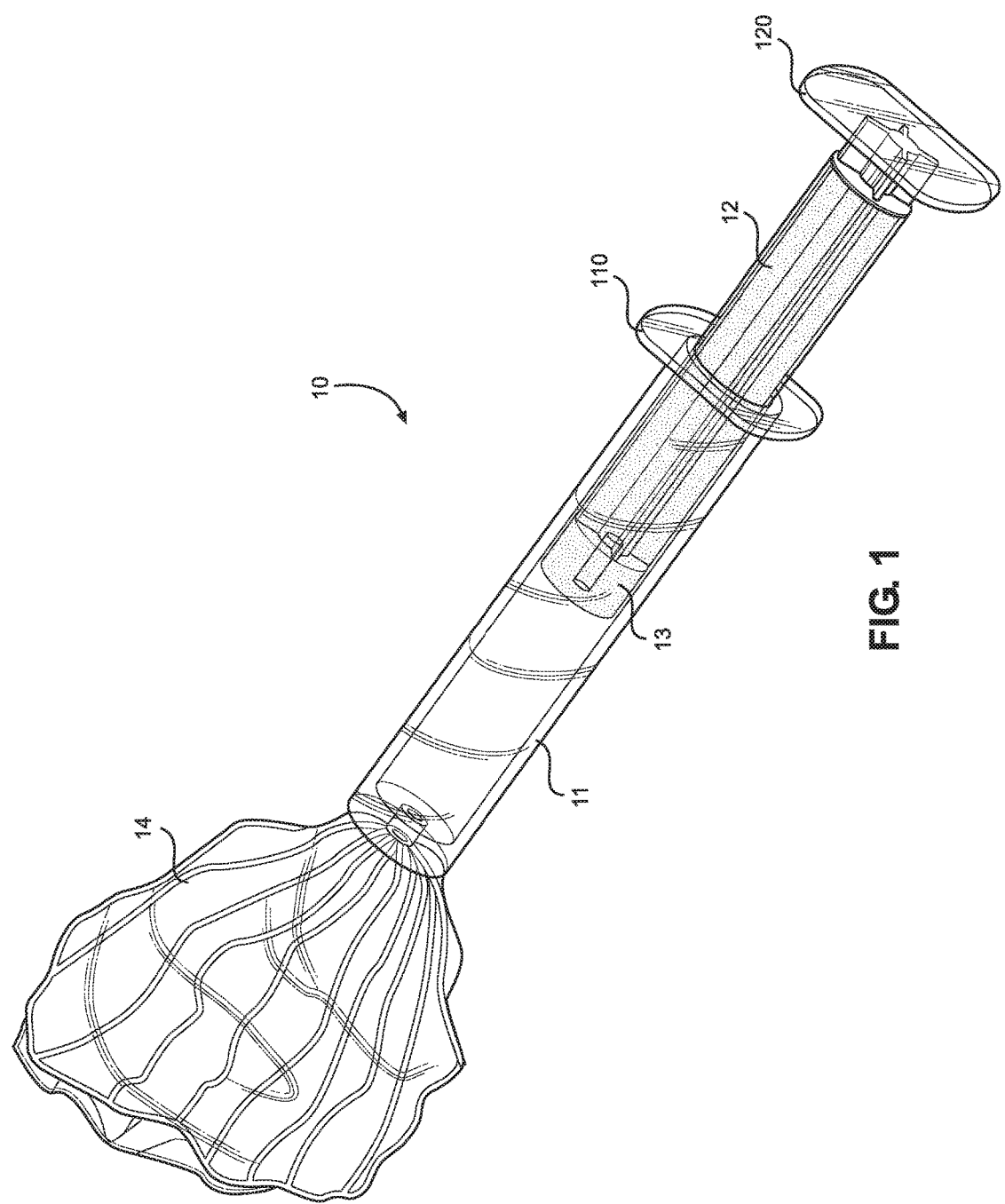
FIG. 1 shows a perspective view of an embodiment of the cervical tissue sample device.

Reference is made herein to the attached drawings. Like reference numerals are used throughout the drawings to depict like or similar elements of the cervical tissue sample device. The figures are intended for representative purposes only and should not be considered to be limiting in any respect.

Referring now to FIG. 1, there is shown a perspective view of an embodiment of the cervical tissue sample device. A cervical tissue sample device 10 comprises a syringe having a plunger 12 slidably disposed within a barrel 11. The barrel 11 has a first end and a second end, such that a longitudinal axis is defined between the first end and the second end. The plunger 12 is configured to slide within the barrel 11, such that the plunger 12 slides along the longitudinal axis of the syringe between the first end of the barrel 11 and the second end of the barrel 11. The first end of the barrel 11 has an opening thereon, such that the plunger 12 can be exposed therethrough when the plunger 12 is fully extended. In the illustrated embodiment, the barrel 11 is transparent, such that an individual can easily view the interior of the barrel 11 and the status of the plunger 12 therein.

The plunger 12 has a first end and a second end, wherein a first end of the plunger 12 has a seal 13 disposed thereon, thereby preventing the collected samples to move past the seal 13. In the illustrated embodiment, the seal 13 is composed of rubber, however in other embodiments the seal 13 comprises any material that can provide a suitably secure seal therearound the first end of the plunger 12. The second end of the plunger 12 has a plunger flange 120 disposed thereon. In the illustrated embodiment, the plunger flange 120 extends outward from the plunger 12 along a lateral axis, wherein the lateral axis is oriented perpendicular to the longitudinal axis. The plunger flange 120 thereby allows the user to grip the plunger 12 more easily and thereby manipulate the plunger 12 through the barrel 11 per the user's desire. Additionally, the plunger flange 120 prevents the loss of the plunger 12 through the barrel 11, such that when the plunger 12 is fully depressed, the plunger flange 120 prevents the plunger 12 from moving further into the barrel 11.

The plunger 12 is configured to move through the barrel 11, such that the syringe moves between an exposed position and a protected position. In the protected position, the plunger flange 120 is extended away from the second end of the barrel 11, such that the seal 13 is adjacent to the second end of the barrel 11. However, in the exposed position, the plunger flange 120 is disposed flush against the second end of the barrel 11, such that the first end of the plunger 12 is aligned with the first end of the barrel 11. In the illustrated embodiment, the second end of the barrel 11 further comprises a barrel flange 110 to aid the user in securely holding the syringe during use.

Figure 2:
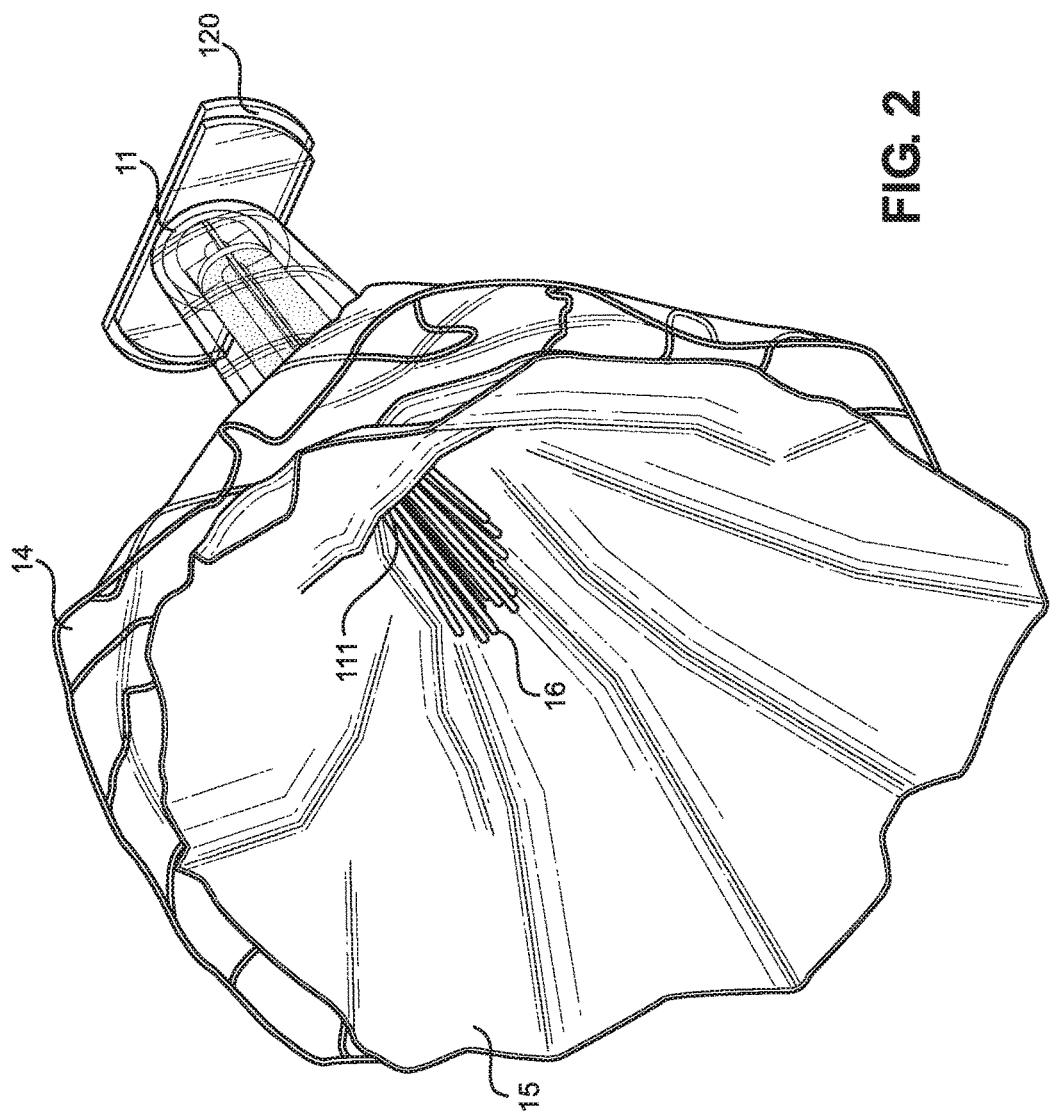
FIG. 2 shows a perspective view of an embodiment of the interior of the cervical tissue sample device in the exposed position.

Referring now to FIG. 2, there is shown a perspective view of an embodiment of the interior of the cervical tissue sample device in the exposed position. A plurality of bristles 16 is secured within the barrel 11, such that when the plunger 12 is actuated, the plurality of bristles 16 extends from the first end of the barrel 11. In the illustrated embodiment, the plurality of bristles 16 are affixed to the seal 13 of the plunger 12, such that when the plurality of bristles 16 are extended they continue to remain affixed to the cervical tissue sample device 10. Additionally, the cervical tissue sample device 10 further includes an outer shroud 14 disposed therearound the plurality of bristles 16. The outer shroud 14 is configured to enclose the plurality of bristles 16 whence exposed from the barrel 11 such that no bristle is accidentally contaminated. In the shown embodiment, the outer shroud 14 further comprises a ribbed membrane to provide additional structural support to the outer shroud 14 when expanded.

In the illustrated embodiment, the plunger flange 120 is flush against the second end of the barrel 11, such that the syringe is in the exposed position. Thus, the plurality of bristles 16 are fully extended from the first end 111 of the barrel 11. The plurality of bristles 16 are dimensioned such that when the plurality of bristles 16 are fully extended from the first end 111, the distalmost tips of each bristle 16 is in contact with the cervix of the user. In this way, the plurality of bristles 16 are configured to capture a sample of cervical tissue by abrading the cervix to capture cells thereon the plurality of bristles 16. In the illustrated embodiment, the plurality of bristles 16 are composed of rubber, such that the plurality of bristles 16 have enough flexibility to accommodate the user once inserted.

An inner shroud 15 extends from a first end 111 of the barrel 11, such that the inner shroud 15 is proximately adjacent to the plurality of bristles 16. The inner shroud 15 is configured to provide immediate protection to the plurality of bristles 16. As noted previously, the outer shroud 14 also extends from the first end 111, such that the outer shroud 14 extends around the inner shroud 15. In the illustrated embodiment, a distal end of the outer shroud 14 extends beyond a distal end of the inner shroud 15, thereby encompassing both the inner shroud 15 and the plurality of bristles 16. Thus, the outer shroud 14 provides additional protection to the plurality of bristles 16, thereby preventing potential contamination to both the inner shroud 15 and the plurality of bristles 16.

In the shown embodiment, both the inner shroud 15 and the outer shroud 14 are shaped similar to an umbrella, wherein the inner shroud 15 and the outer shroud 14 taper outwardly from the first end 111 such that the distal portion of both of the inner and outer shrouds 15, 14 circumscribe the plurality of bristles 16. In this way, the inner and outer shrouds 15, 14 do not interfere with the plurality of bristles 16 when the plurality of bristles 16 is in contact with the cervix.

In the illustrated embodiment, when the syringe is in the protected position, such that the plurality of bristles 16 is disposed within the barrel 11, the outer shroud 14 and the inner shroud 15 are configured to encase the plurality of bristles 16. When the syringe is oriented in the protected position, such that the plurality of bristles 16 are entirely disposed inside the barrel 11 of the syringe, both the inner shroud 15 and the outer shroud 14 are also disposed within the barrel 11, thereby encapsulating the plurality of bristles 16. In the illustrated embodiment, the inner shroud 15 and outer shroud 14 are both configured to collapse around the plurality of bristles 16 as the plurality of bristles 16 is pulled inside the barrel 11 when the plunger is retracted away from the barrel 11. Consequently, both of the inner and outer shrouds 15, 14 are configured to expand outwardly away from the plurality of bristles 16 when the plunger is depressed to expose the plurality of bristles 16.

Figure 3:
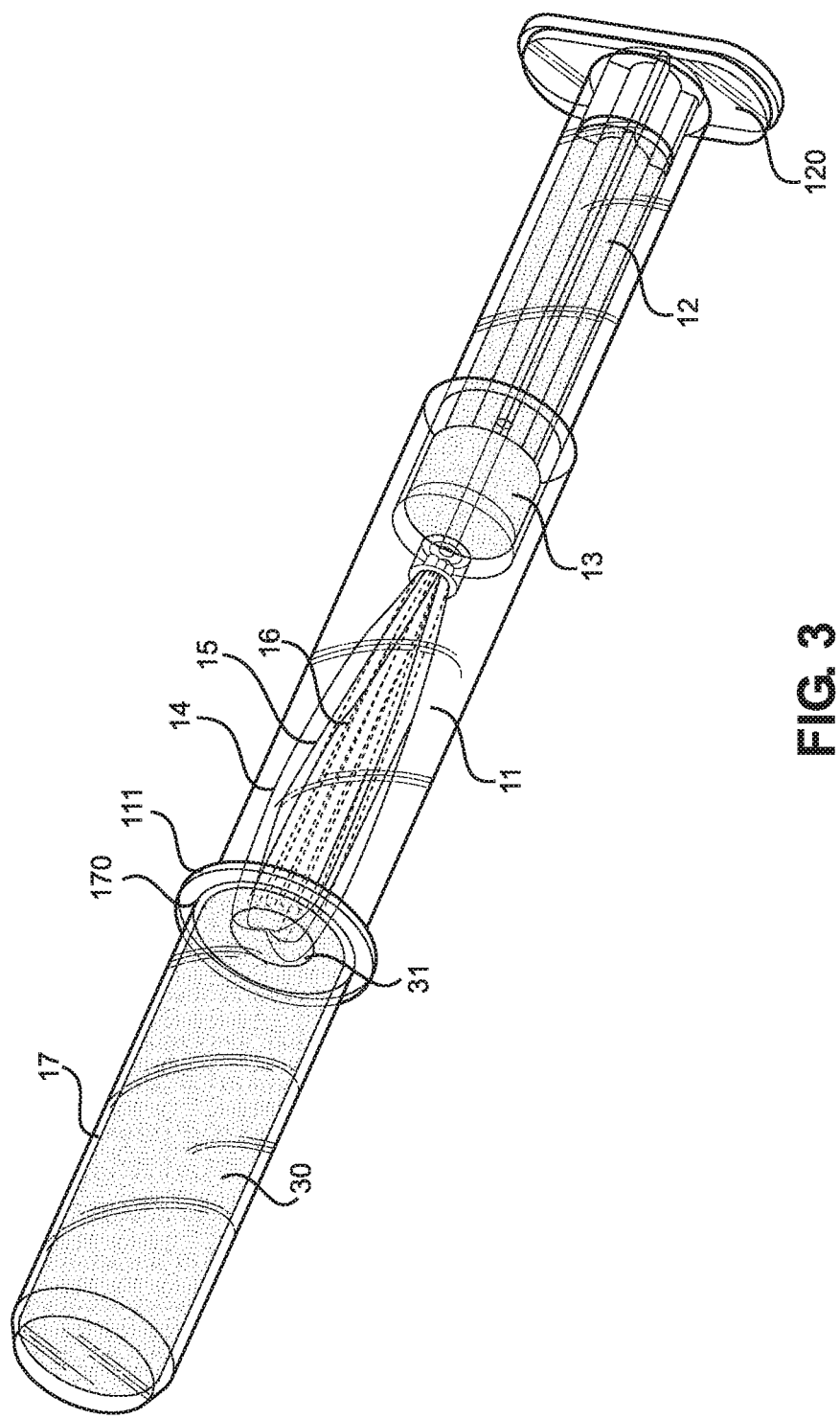
FIG. 3 shows a perspective view of an embodiment of the collection cap atop the cervical tissue sample device.

Referring now to FIG. 3, there is shown a perspective view of an embodiment of the collection cap atop the cervical tissue sample device. In the illustrated embodiment, the cervical tissue sample device further comprises a collection cap 17, configured to removably secure to the first end 111 of the barrel 11, thereby functioning as a lid to secure the contents of the barrel 11, i.e. the material disposed on the plurality of bristles 16. In the illustrated embodiment, the preservative fluid is disposed in a hollow space defined inside the plunger 12. An aqueduct with a one-way valve connects the hollow space in the plunger 12 through the seal, such that fluid may pass through the aqueduct and the one-way valve into the hollow space.

In an alternate embodiment, the seal is removable from the plunger 12 such that the sample collected within the collection cap 17 can be separately sent in to a medical facility for testing. Thus, in the alternate embodiment, the collection cap 17 can function as a hollow tube configured to accept the plurality of bristles 16 therein when the plunger flange 120 is disposed against the second end of the barrel 11. As the plunger 12 is depressed and the plurality of bristles 16 exits the barrel 11, the plurality of bristles 16 enter the collection cap 17. As such, the collection cap 17 is appropriately dimensioned to receive the full length of the plurality of bristles 16 therein. In a further embodiment, the seal 16 is configured to additionally remove from the first end of the plunger 12 to seal the collection cap 17.

Additionally, in the shown embodiment the collection cap 17 further comprises a cap flange 170, thereby providing a flush fit with the first end 111 of the barrel 11 and providing a convenient means of holding the collection cap 17, such that the cap flange 170 prevents the collection cap 17 from slipping between the fingers of the user. Furthermore, in the illustrated embodiment, the outer shroud 14 and the inner shroud 15 are within the barrel 11 attached to the plunger 12 and around the bristles 16.

In operation, a female user desiring a test relating to her cervical cells will utilize the cervical tissue sample device by appropriately positioning the syringe proximate to her vulva with the plunger 12 retracted. The female user is then able to depress the plunger 12 on the syringe such that the plurality of bristles 16 disposed on an opposing end exit a first end of the barrel 11, while one or more shrouds are simultaneously deployed around the plurality of bristles 16 in a reverse umbrella configuration, such that the shrouds open outwards in an reverse umbrella when the plurality of bristles 16 is exposed and enclose around the plurality of bristles 16 when disposed inside the syringe. The female user should continue to depress the plunger 12 until the plurality of bristles 16 is in contact with her cervix. The plurality of bristles 16 having collected a cervix sample, the plunger 12 is again retracted, and the shroud encapsulates the plurality of bristles 16 therein as the plurality of bristles 16 is retracted into the interior body of the barrel 11. In one embodiment, the female user can subsequently affix a collection cap 17 atop the barrel 11 to encase the plurality of bristles 16 therein. In this way, a female is able to comfortably provide cervical cells for a plurality of tests, such as early stage cervical cancer or some STDs (e.g. *chlamydia*, *gonorrhea*, or *HPV*), without leaving home or relying on a medical professional.

It is therefore submitted that the instant invention has been shown and described in various embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A cervical tissue sample device, comprising:
    a syringe, having a plunger slidably disposed within a barrel, wherein the plunger is configured to slide along a longitudinal axis within the barrel;
    the plunger having a first end and a second end, wherein the first end has a seal disposed thereon and the second end comprises a plunger flange;
    a plurality of bristles extending from the seal along the longitudinal axis;
    the barrel having a first end and a second end, wherein the first end has an opening therein such that the plurality of bristles is exposed therethrough when the plunger flange is depressed;
    an outer shroud disposed about a perimeter of the first end of the plunger configured to encapsulate the plurality of bristles therein when the plurality of bristles is disposed within the barrel;
    an inner shroud disposed therearound the plurality of bristles such that the inner shroud is positioned between the plurality of bristles and the outer shroud.

2. The cervical tissue sample device of claim 1, further comprising a barrel flange disposed on the second end of the barrel.

3. The cervical tissue sample device of claim 1, wherein the barrel is transparent.

4. The cervical tissue sample device of claim 1, wherein the first end of the barrel is configured to removably secure to a collection cap.

5. The cervical tissue sample device of claim 4, wherein the collection cap is hollow and dimensioned to receive the plurality of bristles therein to preserve the sample during transport.

6. The cervical tissue sample device of claim 1, further comprising:
    a collection cap having a top end configured to removably secure to the first end of the barrel;
    an interior volume of the collection cap having a preservative fluid therein;
    the top end having a membrane thereon;
    wherein the membrane is configured to puncture when secured to the first end of the barrel such that the barrel is filled with preservative fluid.

* * * * *